United States Patent
Wang et al.

(10) Patent No.: US 11,408,022 B2
(45) Date of Patent: Aug. 9, 2022

(54) PREPARATION METHOD OF ANTI-OXIDATION POLYPEPTIDE

(71) Applicant: Fu Zhou University, Fujian (CN)

(72) Inventors: Shaoyun Wang, Fujian (CN); Xixi Cai, Fujian (CN); Qingyan He, Fujian (CN); Ana Yan, Fujian (CN); Qianwen Ye, Fujian (CN)

(73) Assignee: FU ZHOU UNIVERSITY, Fujian (CN)

( * ) Notice: Subject to any disclaimer, the term of this patent is extended or adjusted under 35 U.S.C. 154(b) by 53 days.

(21) Appl. No.: 16/968,501

(22) PCT Filed: Jul. 19, 2018

(86) PCT No.: PCT/CN2018/096191
§ 371 (c)(1),
(2) Date: Aug. 7, 2020

(87) PCT Pub. No.: WO2020/000536
PCT Pub. Date: Jan. 2, 2020

(65) Prior Publication Data
US 2022/0145349 A1    May 12, 2022

(30) Foreign Application Priority Data
Jun. 26, 2018  (CN) .......................... 20180670285.8

(51) Int. Cl.
*C12P 21/06* (2006.01)
*C07K 7/06* (2006.01)

(52) U.S. Cl.
CPC ................ *C12P 21/06* (2013.01); *C07K 7/06* (2013.01)

(58) Field of Classification Search
CPC .................................. C12P 21/06; C07K 7/06
See application file for complete search history.

(56) References Cited

U.S. PATENT DOCUMENTS

2012/0077747 A1* 3/2012 Anguenot ............ A61K 38/012
435/68.1

OTHER PUBLICATIONS

Weng et al (Journal of Functional Foods II (2014: pp. 342-351, available online Oct. 10, 2014). (Year: 2014).*
Yan et al is related post-filing art and is the inventors own work entitled: "A specific antioxidant peptide: Its properties in controlling oxidation and possible action mechanism", Food Chemistry, vol. 327: pp. 1-9, published online May 6, 2020. (Year: 2020).*
Rodriguez-Diaz et al (Journal of Food Science vol. 76, No. 7, 2011: pages C938-C949) . (Year: 2011).*
Jeevithan et al (Mar. Drugs 2014 vol 12: pp. 3852-3873). (Year: 2014).*

* cited by examiner

*Primary Examiner* — Catherine S Hibbert
(74) *Attorney, Agent, or Firm* — Bayramoglu Law Offices LLC (57) ABSTRACT

A method of preparing an anti-oxidation polypeptide having an amino acid sequence of SEQ ID NO:1 includes enzymatic hydrolysis of black shark skins, which serve as the raw material, with alkali protease, separation, purification, freezing, and drying to obtain the anti-oxidation polypeptide. Enzymatic hydrolysis conditions include 7.0-9.0 pH value, 40-50° C. temperature, 4.0-6.0 h enzymatic hydrolysis time, 2.0-4.0% primer concentration, and 9.0-10.0 wt % of enzymes.

3 Claims, 9 Drawing Sheets

Specification includes a Sequence Listing.

PREPARATION METHOD OF ANTI-OXIDATION POLYPEPTIDE

SEQUENCE LISTING

The instant application contains a Sequence Listing which has been submitted in ASCII format via EFS-Web and is hereby incorporated by reference in its entirety. Said ASCII copy is named GBYC026-POA_Sequence Listing.txt, created on Jan. 27, 2022 and is 511 bytes in size.

TECHNICAL FIELD

The invention provides an anti-oxidation polypeptide and a preparation method thereof, and more specifically relates to an anti-oxidation polypeptide of black shark skins, belonging to the biotechnological field.

BACKGROUND

Oxidation is everywhere in the human life. Free radicals and other active oxygen substances are generated in the process of the cellular metabolism of human bodies. Excessive free radicals generated can destroy cell protective enzymes such as superoxide dismutase, catalase and peroxidase, and even cause apoptosis, for example, by oxidation of cell proteins and membrane lipids.

Super-oxides are generated in foods due to oxidation of nutritive ingredients of foods, which can not only affect the nutritive value of foods, degrade food quality, and in serious cases, sow diseases in human body. For this reason, finding safe antioxidants to inhibit the generation of super-oxides is always a hot topic in bio-nutrition research. Chemical synthetic antioxidants such as BHT and TBHQ, which are better in anti-oxidation effect and lower in price than natural antioxidants, have been widely applied in the food industry.

However, current research shows that synthetic antioxidants have accumulative carcinogenic effects on human organs like livers, spleens and lungs, thereby causing public concerns about safety of the synthetic antioxidants and gradual limitations to their use in food. Therefore, focus is switched to natural antioxidants. A-tocopherol is the most widely applied natural antioxidant, which can effectively keep the stability of oil and fats in food, but is bad for food preservation. Thus, it is necessary to find another safe natural antioxidant.

Over recent years, infectious diseases such as the foot-and-mouth disease and mad cow disease have appeared frequently, and the safety problems of terrestrial animals are growing, so that terrestrial animal proteins and protein products thereof tend to be unsafe for human body; besides, the terrestrial animal proteins are not accepted by many religious people around the world. Therefore, anti-oxidation peptide products prepared using oceanic fish have a broader market prospect. Black shark skins cannot be processed and utilized as a high added-value product (for example, leather product) due to uneven shape and thickness. Study shows that fish skins contain a high content of various proteins, in particular collagen protein (with a content of 60-80%), which is the main ingredient among the fish skin proteins. A great amount of scrap is generated during production and processing of shark products, some of which is used for processing feeds, while the majority is discarded as wastes, not only causing environmental pollution, but also resulting in waste of resources. Thus, how to obtain a highly effective anti-oxidation polypeptide with a specific amino acid sequence from fish skins has become an urgent research subject.

SUMMARY

In order to solve the above problems, the invention provides an anti-oxidation polypeptide and a preparation method thereof for efficiently achieving anti-oxidation activity.

To achieve the above objective, the following technical solution is adopted:

The invention provides an anti-oxidation polypeptide with an amino acid sequence of Gly-Ala-Ala-Val-Ala-Leu (GAAVAL) (SEQ ID NO:1).

The invention provides a preparation method of the anti-oxidation polypeptide, including steps of enzymatic hydrolysis of black shark skins, which serve as the raw material, using alkali protease, separation, purification, freezing and drying to obtain the anti-oxidation polypeptide, wherein enzymatic hydrolysis conditions include: 7.0-9.0 pH value, 40-50° C. temperature, 4.0-6.0 h enzymatic hydrolysis time, 2.0-4.0% primer concentration and 9.0-10.0 wt. % enzymes. Preferably, enzymatic hydrolysis conditions include: 8.0 pH value, 45 C temperature, 4.9 h enzymatic hydrolysis time, 3% primer concentration and 9.6 wt. % enzymes. Separation and purification are completed by using RP-HPLC (reversed-phase high-performance liquid chromatography).

The separation and purification specifically include the following sub-steps:

separating enzymatic hydrolysis products, monitoring the anti-oxidation activity of separated ingredients and collecting ingredients with the maximum anti-oxidation activity by using RP-HPLC, wherein in the process of separation by using the RP-HPLC, an acetonitrile solution in a concentration gradient of 0%-40% that contains 0.05% trifluoroacetic acid (TFA) by volume is used as eluent for linear eluting, and a chromatographic column Gemini 5µ C18 is used to determine the eluent anti-oxidation activity corresponding to each absorption peak, collect and obtain the ingredients with the maximum anti-oxidation activity under the conditions of 100 µL feeding volume, 1 mL/min flow rate and 214 nm detection wavelength. The amino acid sequence of the ingredient is identified using Q-TOF LC-MS. The amino acid sequence of the obtained anti-oxidation polypeptide is Gly-Ala-Ala-Val-Ala-Leu (SEQ ID NO:1).

The specific steps adopted are as follows:

(1) Enzymatic Hydrolysis of Black Shark Skin Proteins

Enzymes were purchased from Novozymes (Tianjin, China).

The black shark skin proteins were enzymatically hydrolyzed under the conditions of 8.0 pH value, 45° C. temperature, 4.9 h enzymatic hydrolysis time, 3% primer concentration and 9.6 wt. % enzymes. 1M NaOH was used to stabilize the pH value. After 5 h hydrolysis, the hydrolysis products were placed in a boiling water bath to deactivate the enzymes for 15 min, and then quickly cooled to room temperature. The cooled substance was put into a centrifuge and then centrifuged at a speed of 4000 r/min for 15 min. Supernatant was kept for later use.

(2) Separation and Purification of Enzymatic Hydrolysis Products

RP-HPLC was adopted to separate enzymatic hydrolysis products, monitor the anti-oxidation activity of separated ingredients, and collect ingredients with the maximum anti-oxidation activity. In the process of separation by using the RP-HPLC, an acetonitrile solution in a concentration gradient of 0%-40% that contained 0.05% trifluoroacetic acid (TFA) by volume was used as eluent for linear eluting, and a chromatographic column Gemini 5µ C18 was used to determine the eluent anti-oxidation activity corresponding to each absorption peak, collect and obtain the ingredients with the maximum anti-oxidation activity under the conditions of 100 µL feeding volume, 1 mL/min flow rate and 214 nm detection wavelength.

(3) Test of Anti-Oxidation Activity

1. ABTS Radical Elimination Activity 7 mM ABTS mother solution and 2.45 mM potassium peroxydisulfate solution were respectively prepared and stored for later use. The two solutions were mixed in a ratio of 1:1 before use. The mixed solution was placed still at room temperature for 16 h, and then diluted with phosphate buffer solution (5 mM, 7.4 pH) to obtain an ABTS radical solution with absorbance of 0.70±0.02 at the wavelength of 734 nm. The ABTS radical solution was mixed with samples of different concentrations and equal volume; after 10 min reaction at room temperature, the absorbance of the mixtures was determined at the wavelength of 734 nm; and finally, the mixtures were zero-set using the phosphate buffer solution (5 mM, 7.4 pH). In the control group, distilled water was used to replace samples. The elimination rate of ABTS radicals of the sample was calculated using the following equation:

$$\text{Elimination rate of } ABTS \text{ radicals } (\%) = \frac{A_{control} - A_{sample}}{A_{control}} \times 100$$

In the equation:
$A_{control}$—absorbance of the control group
$A_{sample}$—absorbance of the sample 2. DPPH Radical Elimination Activity 1 mL of the sample of different concentrations was respectively well mixed with 1 mL of DPPH solution (0.1 mL, prepared using 95% ethanol). The mixed solutions were kept still in shadow at room temperature for 30 min, and then the absorbance was determined at the wavelength of 517 nm. 1 mL of 95% ethanol solution in replacement of the DDPPH solution was used to prepare the sample reference group; and the control group included 1 mL of DPPH solution and 1 mL of 95% ethanol solution. The elimination rate of DPPH radicals of the sample was calculated using the following equation:

$$\text{Elimination rate of } DPPH \text{ radicals } (\%) = \left(1 - \frac{A_i - A_j}{A_0}\right) \times 100$$

In the equation,
$A_i$—absorbance of the sample group
$A_j$—absorbance of the sample reference group
$A_0$—absorbance of the control group 3. Lipid Peroxidation Inhibition Activity 1 mL of sample of different concentrations was respectively placed in a colorimetric tube with a plug. 2 mL of 95% ethanol, 26 µL of linoleic acid and 2 mL of phosphate buffer solution (50 mM, 7.0 pH) were added into each colorimetric tube. The mixed solutions were well mixed and then kept in shadow at a constant temperature of 40° C. In the control group, 1 mL of distilled water was used to replace samples. The peroxidation degree of the mixed solutions was determined every 2 h hours.

The lipid peroxidation level was determined using FTC (ferric thiocyanate method). 100 µL of each mixed solution was well mixed with 4.7 mL of 75% ethanol solution and 0.1 mL of 30% ammonium thiocyanate; 0.1 mL of $FeCl_2$ solution (20 mM, prepared using 3.5% hydrochloric acid solution) was added; each mixture was well mixed and then kept still for accurate 3 min. Then, absorbance was determined at the wavelength of 500 nm.

4. Hydroxyl Radical Elimination Activity 1 mL of the sample was well mixed with 0.3 mL of FeSO4 (8 mM), 1 mL of salicylic acid (3 mM) and 0.25 mL of $H_2O_2$ (20 mM); the mixed solution was kept still at a temperature of 37° C. for 30 min, and then cooled through flowing water; next, 0.45 mL of distilled water was added so that the total volume of the reaction solution reached 3 mL; the reaction solution was centrifuged by 3000 g for 10 min; and the absorbance of the supernatant was determined at the wavelength of 510 nm. Distilled water in replacement of the sample was used to prepare the control group.

$$\text{Elimination rate of hydroxyl radicals } (\%) = \frac{A_{control} - A_{sample}}{A_{control}} \times 100$$

(4) Determination of the Amino Acid Sequence

Determined using Q-TOF LC-MS, the anti-oxidation polypeptide of the invention has a full amino acid sequence of Gly-Ala-Ala-Val-Ala-Leu (SEQ ID NO:1) and a molecular weight of 500 Da.

The invention is aimed to provide a natural and effective antioxidant for the purposes of overcoming defects of the existing natural antioxidants and eliminating public concerns about synthetic antioxidants. By using collagen protein from black shark skins as the raw material, the invention focuses on regulating the enzyme digestion conditions with the aid of alkali protease to obtain an active polypeptide that has a particular peptide chain length and is composed of structural domains, thus effectively achieving antioxidant activity.

The invention changes the concepts and methods of extracting and using existing antioxidants, and eliminates possible side effects of synthetic antioxidants. The invention provides a natural antioxidant, capable of replacing traditional synthetic food oxidants. Moreover, the invention also increases the domestic utilization rate of proteins in aquatic animal skins, not only solves the recycling problems of large amounts of aquatic materials, but also removes customer worries about the food health of antioxidants, which is of profound significance for the development of science and technology, the economy and the food industry.

DETAILED DESCRIPTION OF THE INVENTION

The anti-oxidation polypeptide of the invention has an amino acid sequence of

Gly-Ala-Ala-Val-Ala-Leu.            (SEQ ID NO: 1)

The preparation method is as follows:

Black shark skins which serve as the raw material are enzymatically hydrolyzed using alkali protease; and then the enzymatic hydrolysis products are separated, purified, frozen and dried to obtain the anti-oxidation polypeptide. The enzymatic hydrolysis conditions include: 8.0 pH value, 45 C temperature, 4.9 h enzymatic hydrolysis time, 3% primer concentration and 9.6 wt. % enzymes. RP-HPLC (reversed-phase high-performance liquid chromatography) is used to separate the enzymatic hydrolysis products, monitor the anti-oxidation activity of separated ingredients, and collect ingredients with the maximum anti-oxidation activity. In the process of separation using the RP-HPLC, an acetonitrile solution in a concentration gradient of 0%-40% that contains 0.05% trifluoroacetic acid (TFA) by volume is used as eluent for linear eluting, and a chromatographic column Gemini 5μ C18 is used to determine the eluent anti-oxidation activity corresponding to each absorption peak, collect and obtain the ingredients with the maximum anti-oxidation activity under the conditions of 100 μL feeding volume, 1 mL/min flow rate and 214 nm detection wavelength.

Instruments and test methods adopted in the invention are as follows:

The invention uses the RP-HPLC (reversed-phase high-performance liquid chromatography) to realize efficient separation and purification of the anti-oxidation polypeptide with obvious activity.

Q-TOF LC-MS is used to identify the amino acid sequence of the anti-oxidation polypeptide.

In order to further clarify the content, features and effects of the invention, the following embodiment is described below as an example:

Embodiment 1

3 g of black shark skins were weighed and added into 100 ml of de-ionized water; and then 1 mol/L NaOH was added to adjust the pH value of the solution to 8.0. The solution was heated to reach a temperature of 45° C. in a water bath first, and then added with corresponding enzymes by a ratio of 9.6 wt. %. The enzymatic hydrolysis time was 4.9 hours. Next, the solution was placed in a boiling water bath to deactivate enzymes for 15 min, cooled, and centrifuged at a speed of 4000 rpm for 15 min. The supernatant was collected for later use.

Figure 1:
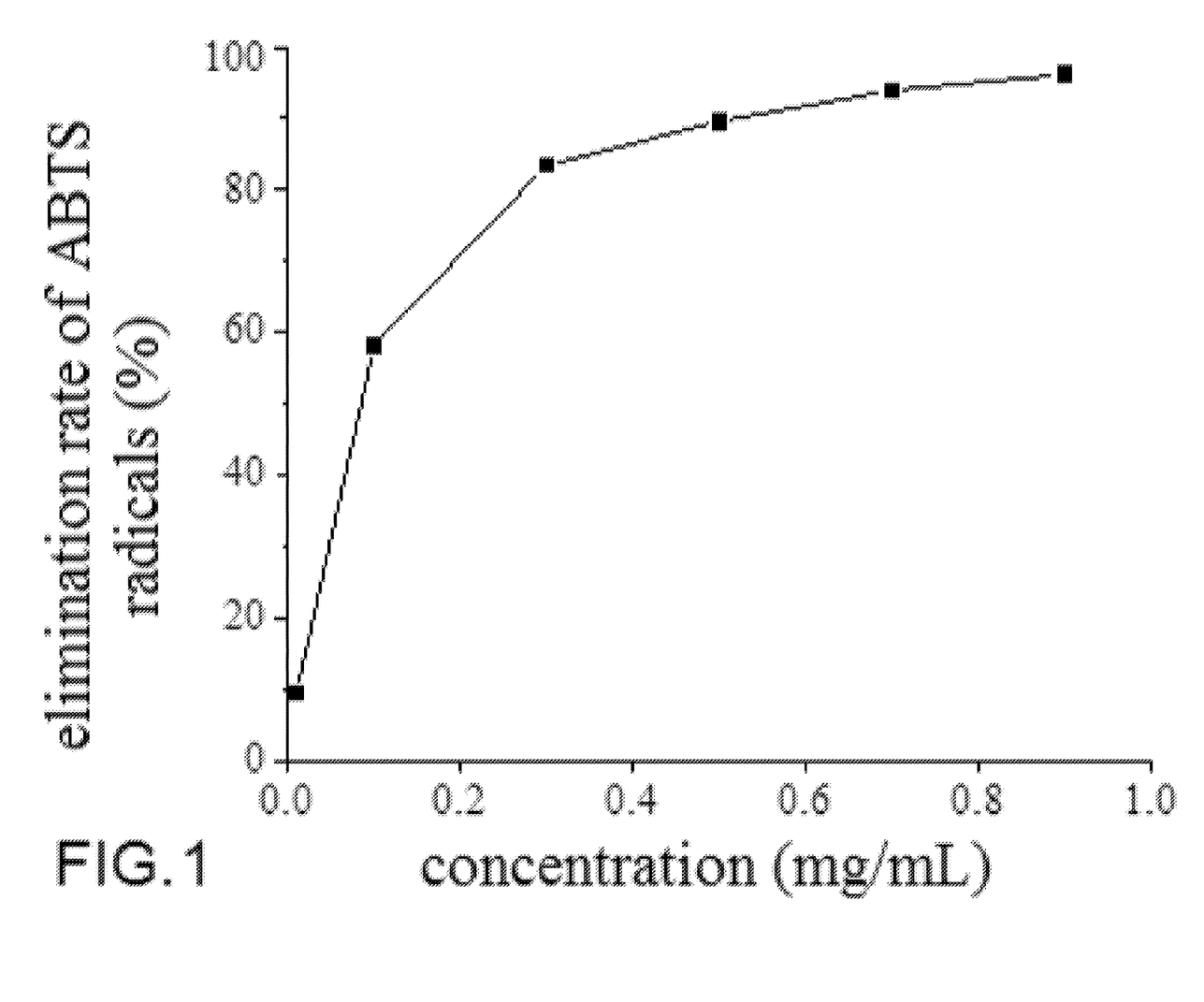
FIG. 1 is a curve diagram of the ABTS radical elimination rate of the FIG. 1 is a curve diagram of the ABTS radical elimination rate.
Figure 2:
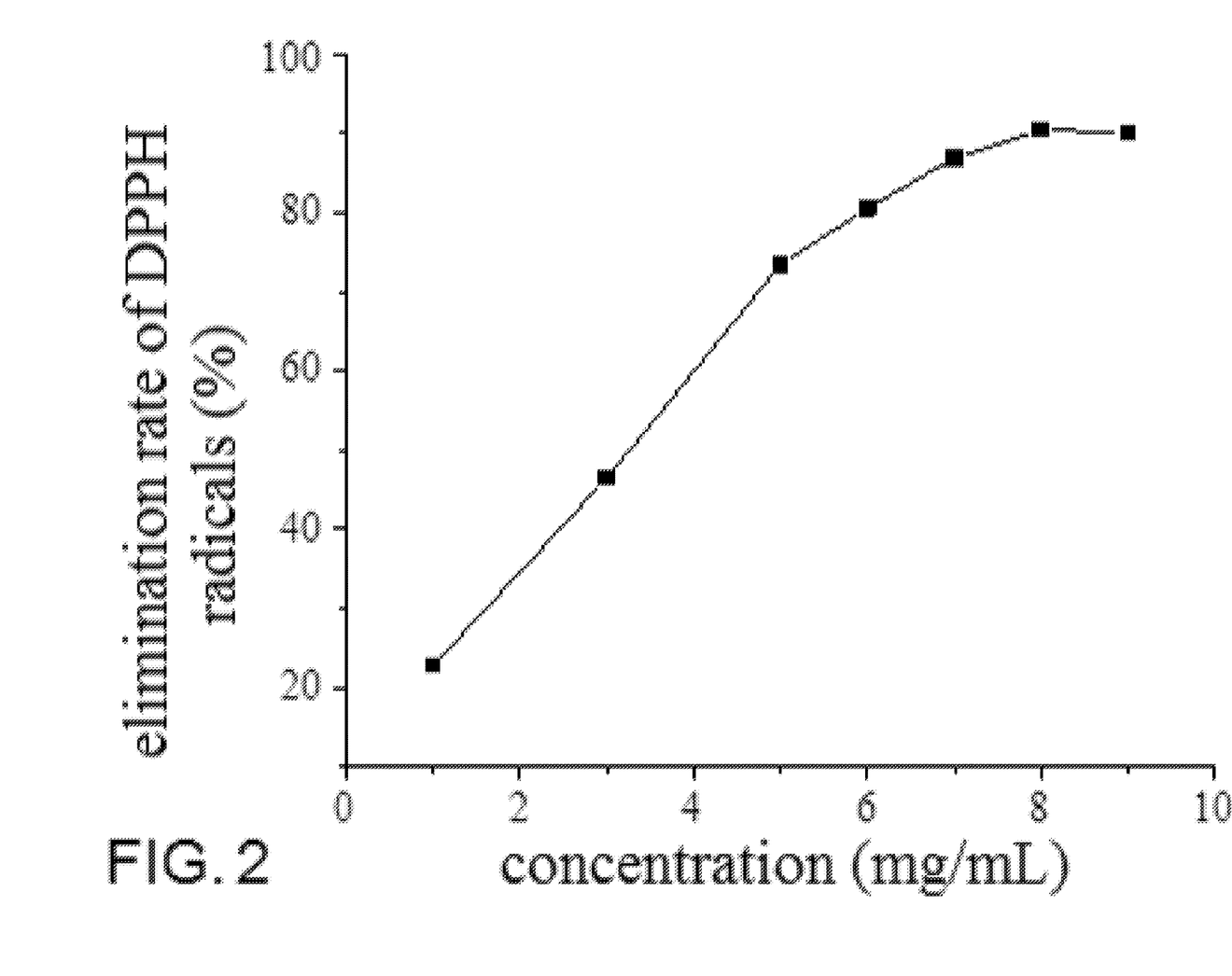
FIG. 2 is a curve diagram of the DPPH radical elimination rate of the protease hydrolysate of black shark skins.
Figure 3:
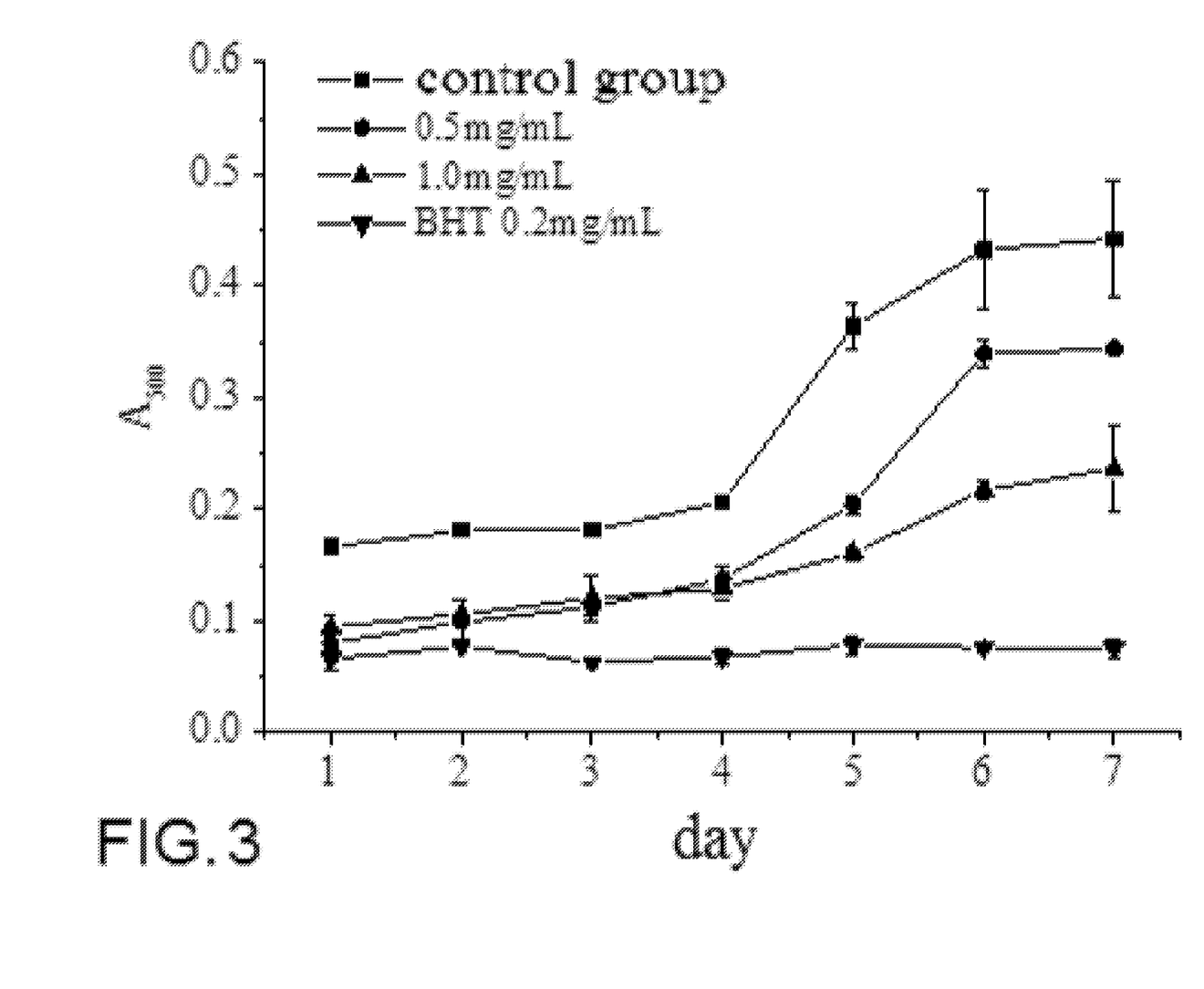
FIG. 3 is a diagram of the lipid peroxidation inhibition activity of the protease hydrolysate of black shark skins.
Figure 4:
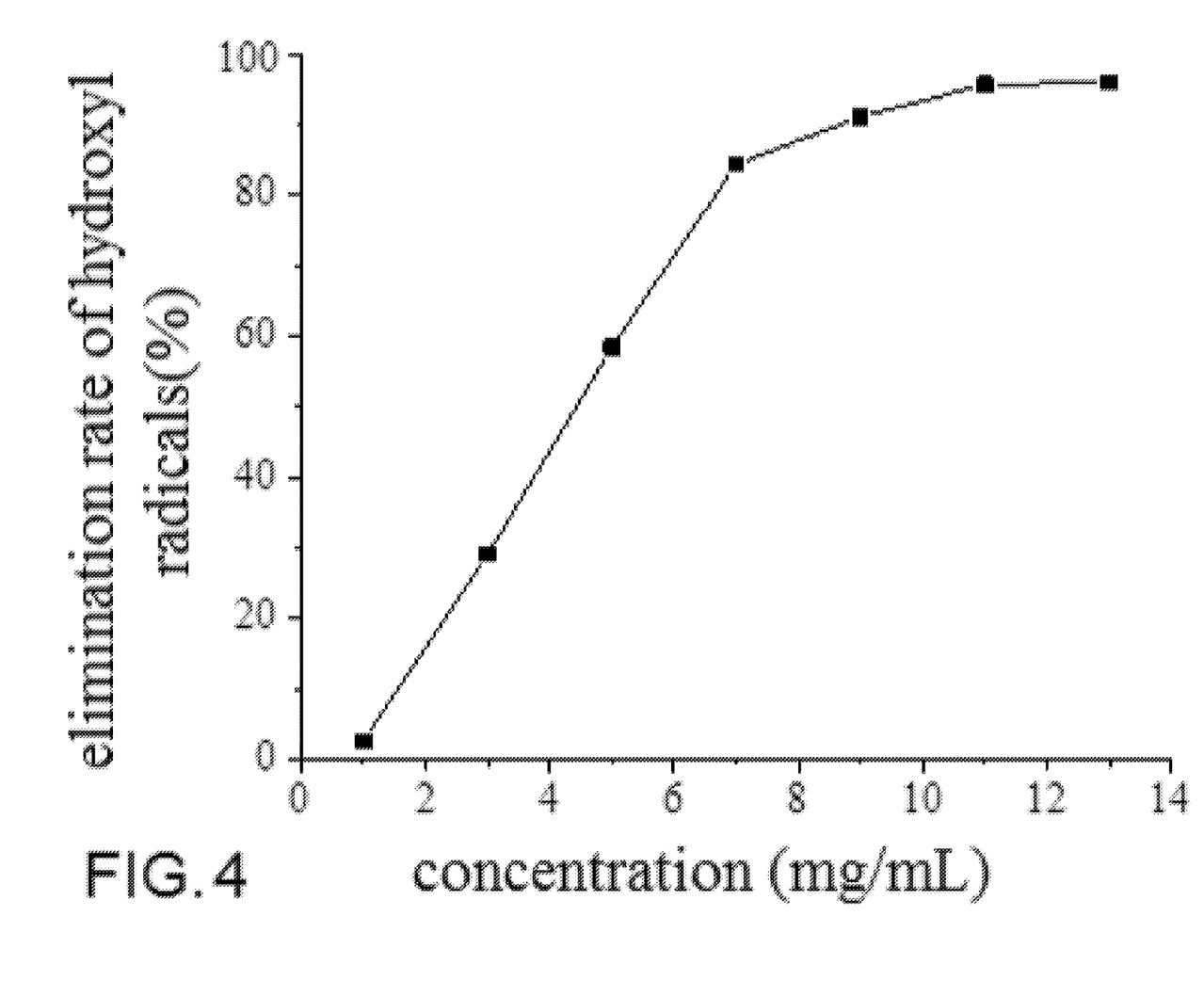
FIG. 4 is a curve diagram of the hydroxyl radical elimination rate of the protease hydrolysate of black shark skins.

The anti-oxidation activity of the prepared enzymatic hydrolysis product of black shark skins was identified, wherein the inhibitory concentration 50% of ABTS was 80 μg/mL (as shown in FIG. 1), the inhibitory concentration 50% of DPPH was 3.19 mg/mL (as shown in FIG. 2), and the product had certain lipid peroxidation inhibition activity (as shown in FIG. 3) and hydroxyl radical elimination activity (as shown in FIG. 4). Therefore, the enzymatic hydrolysis product of black shark skins has certain anti-oxidation activity.

Figure 5:
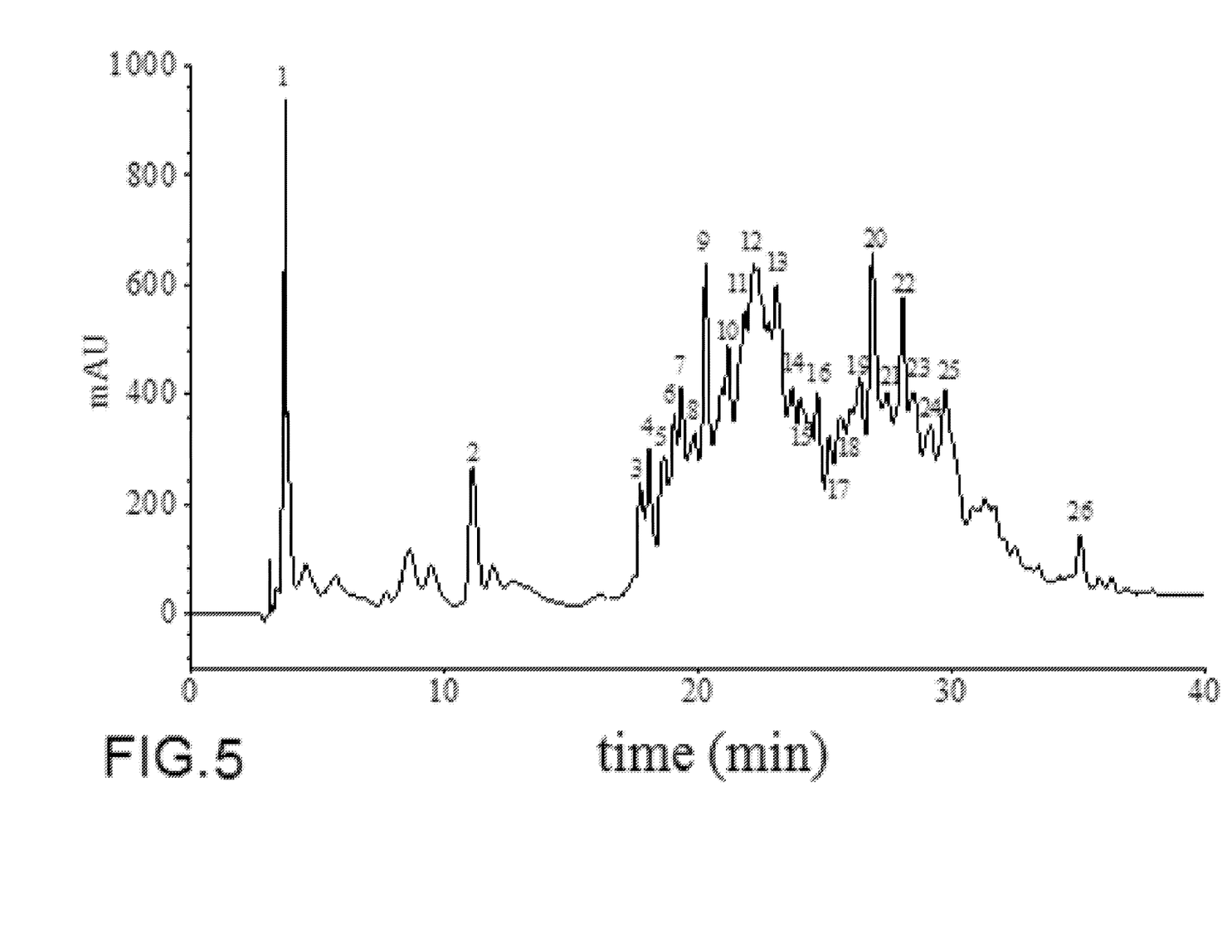
FIG. 5 is a RP-HPLC elution diagram of the protease hydrolysate of black shark skins.
Figure 6:
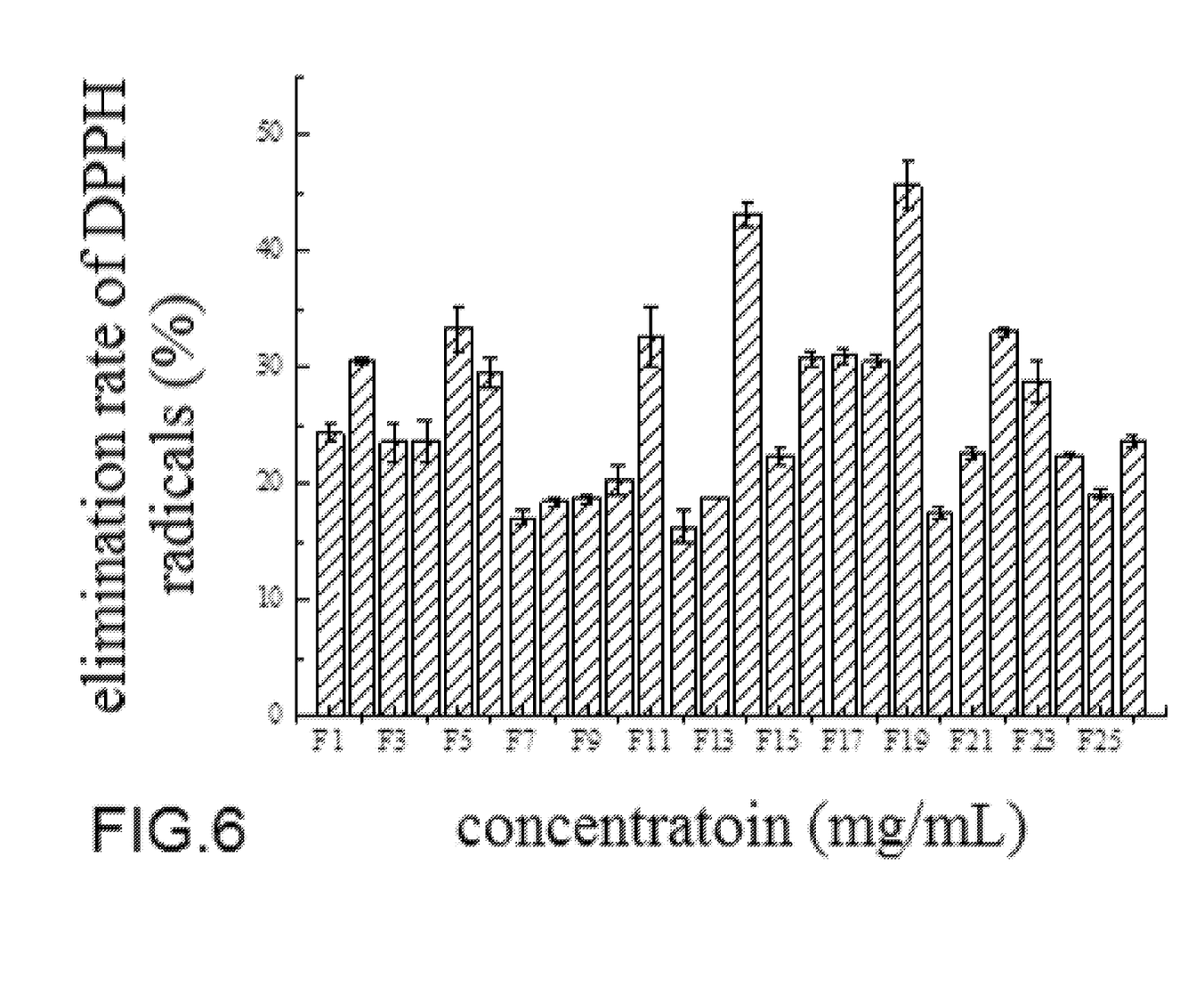
FIG. 6 is the curve diagram of the DPPH radical elimination rate of the RP-HP LC eluting ingredient of the protease hydrolysate of black shark skins.

RP-HPLC was adopted to separate enzymatic hydrolysis products (as shown in FIG. 5), monitor the anti-oxidation activity of separated ingredients, and collect ingredients with the maximum anti-oxidation activity. In the process of separation using the RP-HPLC, the acetonitrile solution in a concentration gradient of 0%-40% that contained 0.05% trifluoroacetic acid (TFA) by volume was used as eluent for linear eluting, and the chromatographic column Gemini 5μ C 18 was used to determine the eluent anti-oxidation activity corresponding to each absorption peak, collect and obtain the ingredient F19 with the maximum anti-oxidation activity under the conditions of 100 μL feeding volume, 1 mL/min flow rate and 214 nm detection wavelength (as shown in FIG. 6).

Figure 7:
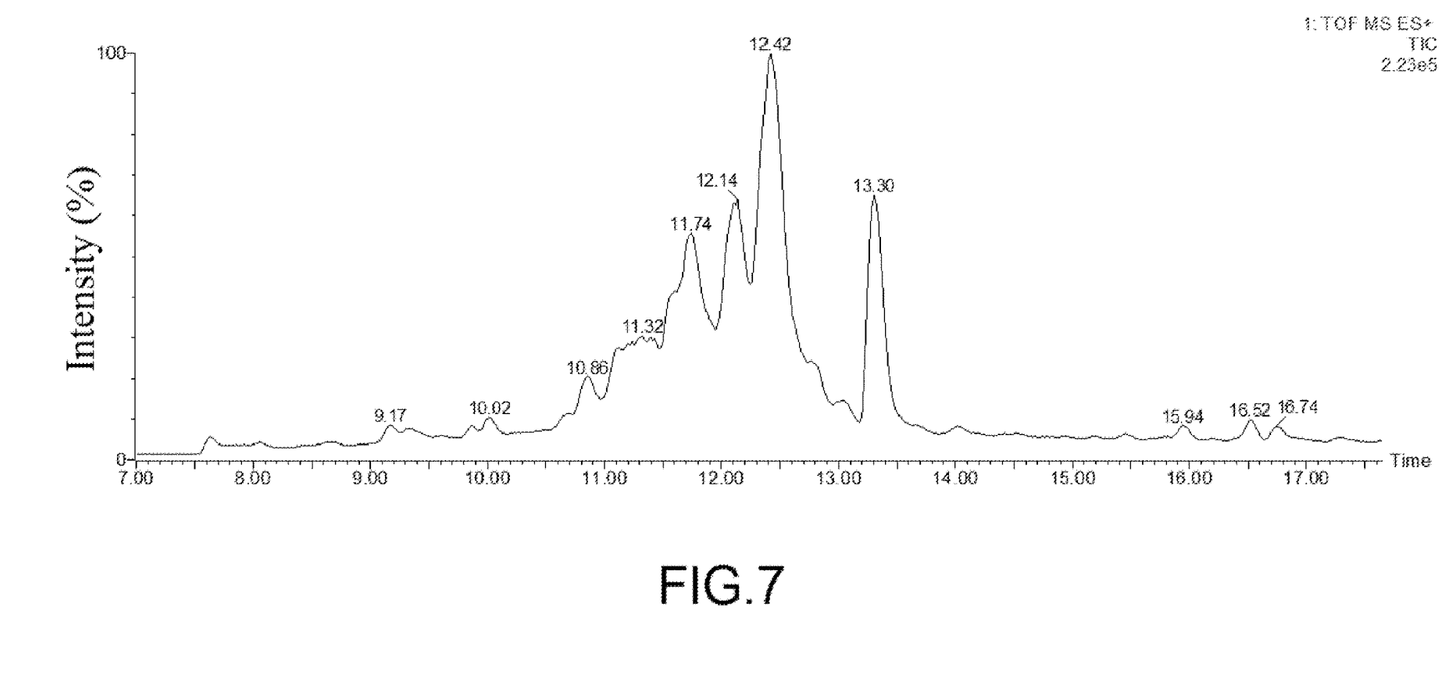
FIG. 7 is a total ions chromatogram of F19.
Figure 8:
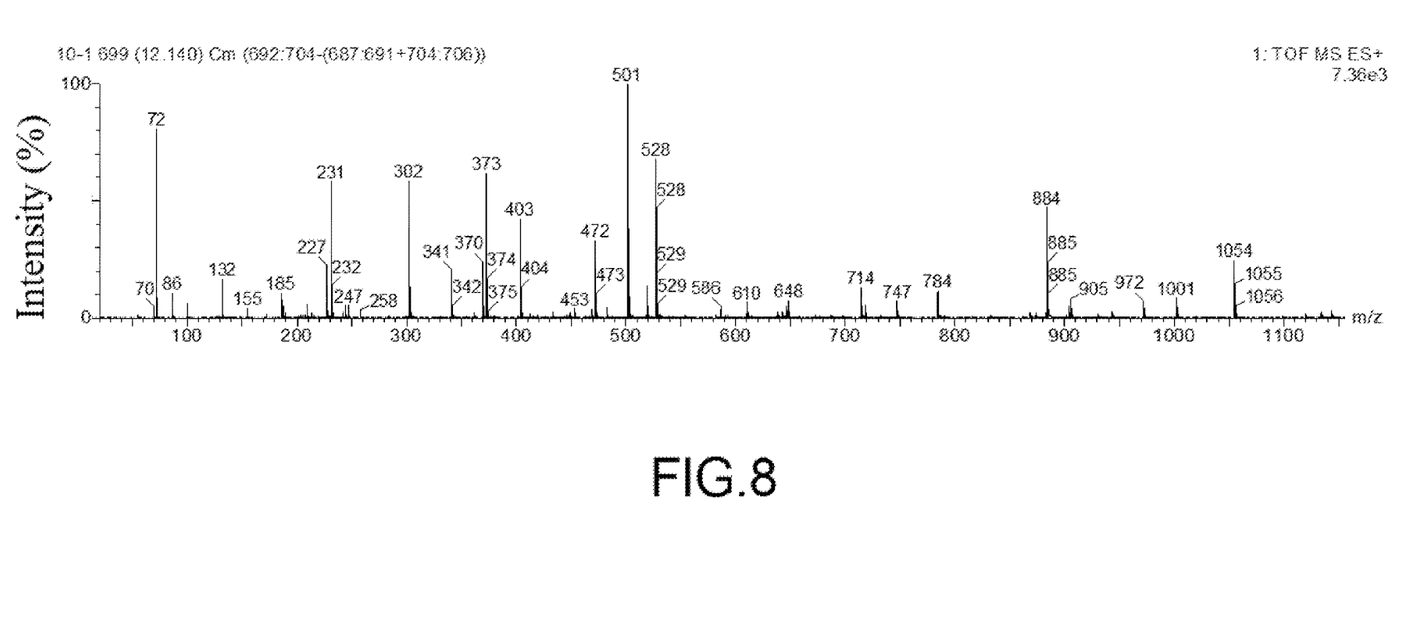
FIG. 8 is a grade-1 mass chromatogram of the anti-oxidation polypeptide.
Figure 9:
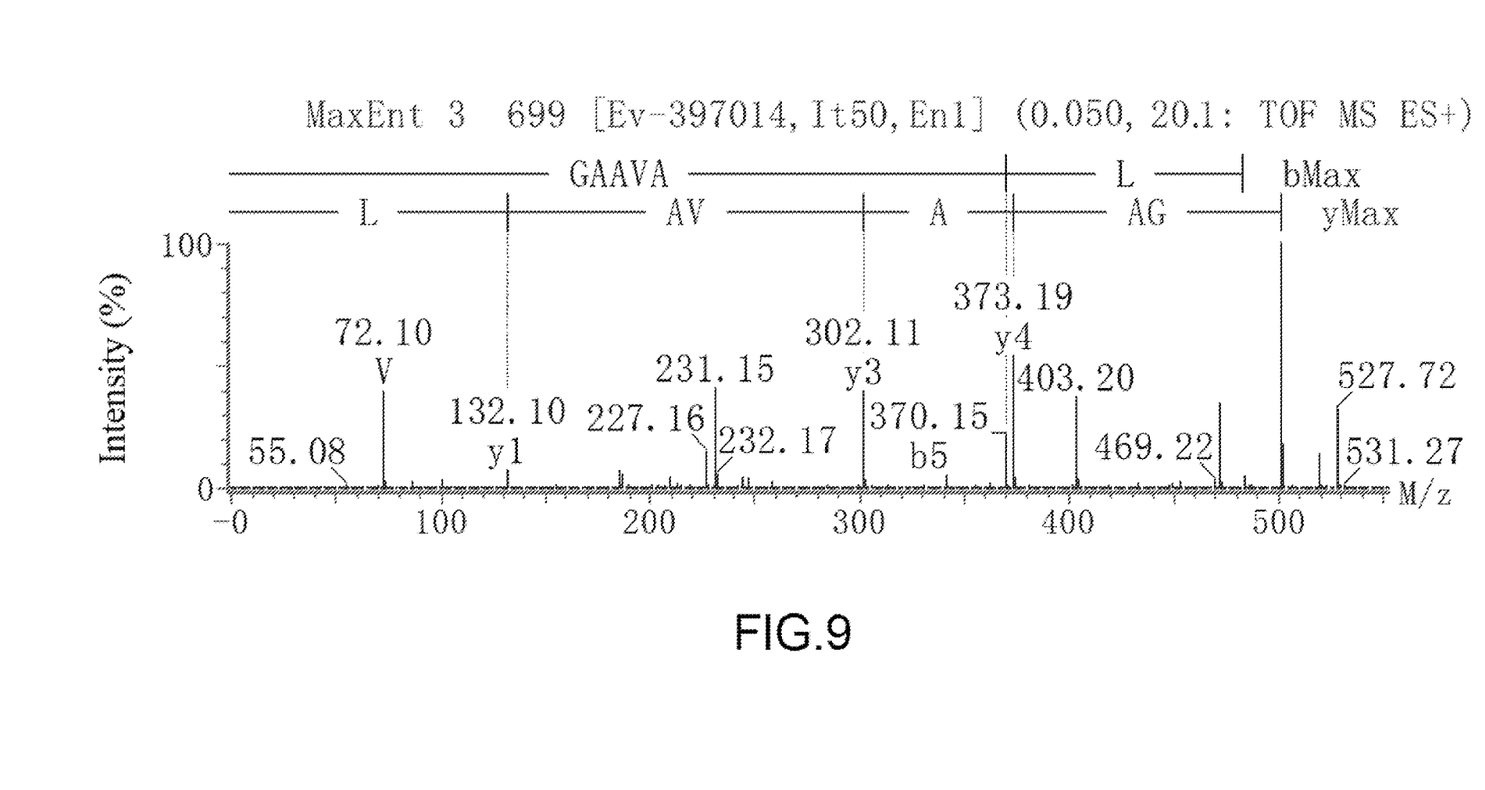
FIG. 9 is a grade-2 mass chromatogram of the anti-oxidation polypeptide.

Ingredient F19 was identified using Q-TOF LC-MS (see table 1 and table 2 for the chromatographic conditions and mass spectrum conditions). The total iron flow chart of F19 can be seen in FIG. 7. Then, 12.14 min ion peak was determined using MS/MS grade-2 chromatogram to obtain the full amino acid sequence (as shown in FIGS. 8-9) of Gly-Ala-Ala-Val-Ala-Leu (SEQ ID NO:1) (molecular weight: 500 Da), namely the anti-oxidation polypeptide of the invention. The anti-oxidation activity (as shown in table 3) of anti-oxidation polypeptide was determined, wherein the elimination rate of ABTS radicals was (64.12±0.20)%, the elimination rate of DPPH radicals was (67.00±0.24)%, and the oxygen radical absorption capacity was (527.53±65.15) μmol Trolox/g peptide.

TABLE 1

Parameters of chromatographic conditions for F19 identification

| Item | Chromatographic conditions F19 |
|---|---|
| Mobile phase | 100% acetonitrile-0.1% acetic acid |
| Flow rate | 0.4 mL/min |
| Detection wavelength | 214 nm |
| Chromatographic column | Gemini C18 (10 × 250 mm, 5 μ) |
| Detector | UV |

TABLE 2

Parameters of mass spectrum conditions for F19 identification

| Item | MS conditions F19 |
|---|---|
| Ion mode | ESI$^+$ |
| Capillary voltage | 35 k Volts |
| Desolvation temperature | 400° C. |
| Collision energy | 6 eV |
| Mass range | 50-2000 Da |
| Ionization temperature | 100° C. |

TABLE 3

Anti-oxidation activity of the anti-oxidation polypeptide

| Elimination rate of ABTS radicals (%) (1 mg/mL) | Elimination rate of DPPH radicals (%) (1 mg/mL) | Oxygen radical absorption capacity (μmol Trolox/g peptide) |
|---|---|---|
| 64.12 ± 0.20 | 67.00 ± 0.24 | 527.53 ± 65.15 |

The above is merely preferable embodiment of the invention. All equivalent changes and modifications made on the basis of the invention shall fall within the protective scope of the invention.

What is claimed is:

1. A method of preparing an anti-oxidation polypeptide having an amino acid sequence of SEQ ID NO:1, comprising the steps of:
   (a) enzymatically hydrolysing black shark skins using alkali protease enzymes;
   (b) separating the enzymatically hydrolysed black shark skins to obtain a plurality of enzymatic hydrolysis products;
   (c) purifying the enzymatic hydrolysis products;
   (d) freezing the enzymatic hydrolysis products; and
   (e) drying the enzymatic hydrolysis products to obtain an anti-oxidation polypeptide;
   wherein step (a) is taken under a plurality of conditions including 7.0-9.0 pH value, 40-50° C. temperature, 4.0-6.0 h enzymatic hydrolysis time, 2.0-4.0% primer concentration, and 9.0-10.0 wt % of alkali protease enzymes.

2. The method of claim 1, step (b) further comprising the sub-steps of:
   (b-1) separating a plurality of ingredients of the enzymatic hydrolysis products;
   (b-2) monitoring an anti-oxidation activity of the ingredients; and
   (b-3) collecting the ingredients having a maximum anti-oxidation activity by means of RP-HPLC (reversed-phase high-performance liquid chromatography);
   wherein in sub-step (b-3) an acetonitrile solution having a concentration gradient of 0%-40% containing 0.05% trifluoroacetic acid (TFA) by volume is used as eluent for linear eluting, and a chromatographic column Gemini 5μ C18 is used to determine an eluent antioxidant activity corresponding to each of a plurality of absorption peaks, and the ingredients having the maximum anti-oxidation activity under a plurality of conditions including 100 μL feeding volume, 1 mL/min flow rate, and 214 nm detection wavelength are collected.

3. The method of claim 1, wherein the amino acid sequence of SEQ ID NO:1 is identified by means of Q-TOF LC-MS.

* * * * *

SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Anti-oxidation peptide

<400> SEQUENCE: 1

Gly Ala Ala Val Ala Leu
1               5